(12) United States Patent
Van Wetering et al.

(10) Patent No.: US 10,064,923 B2
(45) Date of Patent: Sep. 4, 2018

(54) THERAPEUTIC CANCER VACCINES DERIVED FROM A NOVEL DENDRITIC CELL LINE

(71) Applicant: DCPRIME B.V., Leiden (NL)

(72) Inventors: Sandra Van Wetering, Leidschendam (NL); Adriana Marie Kruisbeek, Amsterdam (NL)

(73) Assignee: DCPRIME B.V., Leiden (NL)

( * ) Notice: Subject to any disclaimer, the term of this patent is extended or adjusted under 35 U.S.C. 154(b) by 362 days.

(21) Appl. No.: 14/648,210

(22) PCT Filed: Dec. 10, 2013

(86) PCT No.: PCT/EP2013/076067
§ 371 (c)(1),
(2) Date: May 28, 2015

(87) PCT Pub. No.: WO2014/090795
PCT Pub. Date: Jun. 19, 2014

(65) Prior Publication Data
US 2015/0297698 A1 Oct. 22, 2015

(30) Foreign Application Priority Data
Dec. 11, 2012 (EP) .................... 12196496

(51) Int. Cl.
| | | |
|---|---|---|
| *C12N 5/00* | (2006.01) | |
| *C12N 5/02* | (2006.01) | |
| *A61K 39/00* | (2006.01) | |
| *C12N 5/0784* | (2010.01) | |
| *A61K 35/15* | (2015.01) | |

(52) U.S. Cl.
CPC .......... *A61K 39/0011* (2013.01); *A61K 35/15* (2013.01); *C12N 5/0639* (2013.01); *A61K 2039/5154* (2013.01); *C12N 2501/02* (2013.01); *C12N 2501/22* (2013.01); *C12N 2501/2301* (2013.01); *C12N 2501/2304* (2013.01); *C12N 2501/2306* (2013.01); *C12N 2501/25* (2013.01); *C12N 2501/999* (2013.01); *C12N 2506/11* (2013.01)

(58) Field of Classification Search
None
See application file for complete search history.

(56) References Cited

U.S. PATENT DOCUMENTS
2013/0274134 A1  10/2013  Lindstedt et al.

FOREIGN PATENT DOCUMENTS
WO   2012056236 A2   5/2012
WO   2014090795 A1   6/2014

OTHER PUBLICATIONS

Aerts-Toegaert et al., 2007, Eur. J. Immunol. vol. 37: 686-695.*
Clinical trials.gov, Leukemic Dendritic Cell Vaccination in Patients With Acute Myeloid Leukemai, received May 30, 1011, pp. 1-5.*
Wlodarska et al., 1997, Blood. vol. 89: 1716-1722.*
Rosenfeld et al., 2003, Leukemia, vol. 17: 1301-1312.*
PCT International Preliminary Report on Patentability, PCT/EP2013/076067, dated Jun. 15, 2015.
Erben et al., "CS-1, A Novel c-kit hi+ Acute Myeloid Leukemia Cell Line with Dendritic Cell Differentiation Capacity and Absent Immunogenicity," International Journal of Cancer, John Wiley & Sons, Inc. New York, NY, US, Jun. 10, 2003, pp. 232-240, vol. 105, No. 2.
Kruisbeek, Ada, "Adoption of Cryostor® in Manufacturing of a Dendritic Cell Vaccine Platform," Biopreservation Today, 2011, p. 10, vol. 3, No. 1.
Moldenhauer et al., Tumor Necrosis Factor Alpha-Stimulated Endothelium: An Inducer of Dendritic Cell Development from Hematopoietic Progenitors and Myeloid Leukemic Cells, Stem Cells, Mar. 1, 2004, pp. 144-157, vol. 22, No. 2.
Van De Ven et al., "Exposure of CD34+ precursors to cytostatic anthraquinone-derivatives induces rapid dendritic cell differentiation: implications for cancer immunotherapy," Cancer Immunology, Immunotherapy, Springer, Berlin, DE, Aug. 27, 2011, pp. 181-91, vol. 61, No. 2.
PCT International Search Report and Written Opinion for PCT/EP2013/076067 dated Feb. 5, 2014.

* cited by examiner

*Primary Examiner* — Amy E Juedes
(74) *Attorney, Agent, or Firm* — Patent Law Works LLP

(57) ABSTRACT

The invention is in the field of medical sciences. It provides means and methods for the treatment of cancer. More in particular, it provides cells and cell lines that can be developed into fully functional dendritic cells. These cells endogenously express cancer-specific antigens, which makes them particularly suited for the treatment of different kinds of cancer. More in particular, the invention relates to a precursor cell line for dendritic cells called DC-One as deposited at the DSMZ under accession number DSMZ ACC3189 on Nov. 15, 2012.

3 Claims, 11 Drawing Sheets

THERAPEUTIC CANCER VACCINES DERIVED FROM A NOVEL DENDRITIC CELL LINE

FIELD OF THE INVENTION

Figure 1:
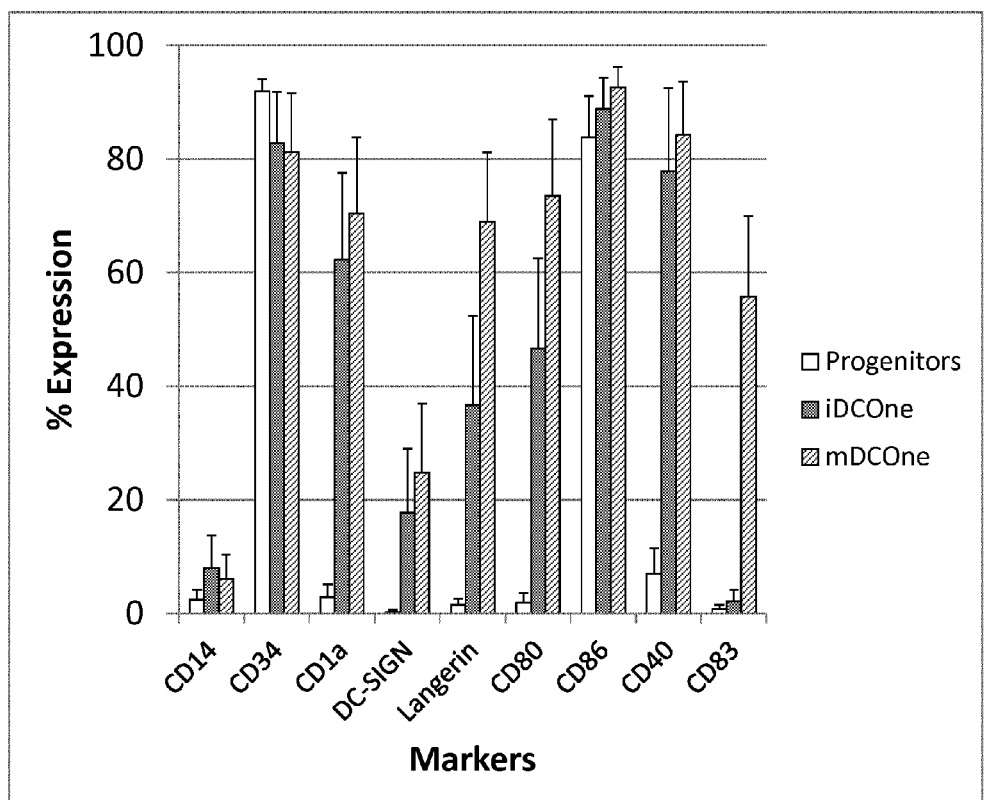

The invention is in the field of medical sciences. It provides means and methods for the treatment of cancer. More in particular, it provides cells and cell lines that can be developed into fully functional dendritic cells. These cells endogenously express cancer-specific antigens, which makes them particularly suited for the treatment of different kinds of cancer.

BACKGROUND OF THE INVENTION

Dendritic cells (DCs) belong to the bone marrow-derived cell lineage, are present throughout the body in multiple tissues, and function as the central part of the mammalian immune system. Their main function is to process antigen material and present it on their surface to other cells of the immune system. Thus, dendritic cells function as antigen-presenting cells (APCs), and they do so more efficiently than any other type of APC, such as macrophages. DCs also act as messengers between innate and adaptive immunity, through a range of cell surface receptors that capture microbes and trigger information which is then transmitted to lymphocytes and cells of the innate immunesystem.

Dendritic cells are present in tissues that are in direct contact with the external environment, such as the skin (where there is a specialized dendritic cell type called Langerhans cells) and the inner lining of the nose, lungs, stomach and intestines. They can also be found in an immature state (iDCs) in the blood. Once activated, they migrate to the lymph nodes where they interact with T cells and B cells to initiate and shape the adaptive immune response. At certain development stages, they grow branched projections, the dendrites, that give the cell its name (déndron being Greek for "tree"). While similar in appearance, these are structures that can be distinguished from the dendrites of neurons.

Three types of DCs have been defined in human blood and these are the CD1C+ myeloid DCs, the CD141+ myeloid DCs and the CD303+ plasmacytoid DCs. This represents the nomenclature proposed by the IUIS nomenclature committee. In dendritic cells belonging to the myeloid lineage, the similar morphology results in a very large contact surface to their surroundings, compared to overall cell volume. Plasmacytoid DC have a more rounded shape, comparable to plasma cells.

Myeloid dendritic cells are made up of at least two subsets that can be distinguished by the reciprocal expression of CD141 (also known as BCDA3) and CD1C (also know as BDCA1). CD141-expressing DC represent the more common myeloid cells, often referred to as DC-1, and these cells represent major stimulator of the CD8 T cell response. The extremely rare myeloid CD1C expressing DC is often referred to as DC-2, and its function continues to be analyzed and defined. It has been reported to have a function in combating wound infection. Myeloid DC-1 cells express MHC class I and II molecules for antigen presentation, and a range of other molecules relevant for interacting with both the innate and the adaptive immune system. They can also secrete multiple cytokines, including IL-12, and express various kinds of Toll-like receptors (TLR) such as TLR2 and TLR4.

Plasmacytoid dendritic cells resemble plasma cells in appearance, but have certain functional characteristics similar to myeloid dendritic cells. They can produce high amounts of interferon-alpha and thus became known as IPC (interferon-producing cells) before their dendritic cell nature was revealed. Plasmacytoid dendritic cells express TLR7 and TLR9, and can be distinguished form myeloid DC by the expression of CD303, also known as BDCA-2.

Lymphoid and myeloid DCs evolve from lymphoid or myeloid precursors respectively and thus are both of hematopoietic origin. The blood DCs are typically identified and enumerated through antibodies that specifically bind to certain markers, and antibody-binding can be detected by flow cytometry through fluorescent and other markers attached to the antibodies.

Dendritic cells are derived from hematopoietic bone marrow progenitor cells, and these progenitor cells initially transform into immature dendritic cells (iDCs). These immature cells are characterized by high endocytic activity, in keeping with their efficient capture of antigens, and in this stage, their ability to activate T-cells is still poor. This coincides with low expression of co-stimulatory molecules and limited ability to secrete certain cytokines. Immature dendritic cells constantly sample the surrounding environment for pathogens such as viruses and bacteria. This is done through pattern recognition receptors (PRRs) such as the TLRs. TLRs recognize specific chemical signatures found on subsets of pathogens and tumour tissue. Immature dendritic cells may also phagocytose small quantities of membrane from live cells, in a process called nibbling.

Once they have come into contact with antigens presented by the environment (such as microbes or tumor cells), immature dendritic cells are triggered to differentiate into mature dendritic cells and begin to migrate to the lymph nodes. Immature dendritic cells phagocytose pathogens and degrade their proteins into small pieces, and upon maturation present those fragments at their cell surface using MHC molecules. Simultaneously, they up-regulate cell-surface receptors that act as co-receptors in T-cell activation such as CD83, CD40 and others, thus greatly enhancing their ability to activate T-cells. In addition, they up-regulate, a chemotactic receptor that induces the dendritic cell to travel through the blood stream to the spleen or through the lymphatic system to lymph nodes. Here they act as antigen-presenting cells: they activate helper T-cells and killer T-cells as well as B-cells by presenting them with antigens derived from pathogens or tumors, alongside non-antigen specific co-stimulatory signals.

Every T-cell is specific to one particular antigenic peptide presented in MHC class I or II molecules, through receptors that are clonally expressed and are termed T cell receptors (TCRs). Only dendritic cells, are able to activate resting naïve T-cells when the matching antigen-MHC complex is presented to their particular TCR. Other antigen presenting cell types, such as macrophages and B cells, do not have the ability to trigger native resting T cells, and can only activate memory T cell. Because dendritic cells can activate both memory and naive T cells, they are often refereed to as professional antigen-presenting cells, and they are the most potent of all the antigen-presenting cells.

Myeloid DC can be generated from monocytes, white blood cells which circulate in the body and, depending on the right signal, can turn into either dendritic cells or macrophages. The monocytes in turn are formed from stem cells in the bone marrow. Monocyte-derived dendritic cells can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) further differentiates the iDCs into mature dendritic cells.

Dendritic cells are constantly in communication with other cells in the body. This communication can take the form of direct cell-to-cell contact based on the interaction of cell-surface proteins. An example of this includes the interaction of the membrane proteins of the B7 family of dendritic cells, CD80 (B7.1) and CD86 (B7.2), with CD28 and CTLA4 on T cells. In addition, cellular communication of DC with their environment takes place over a distance via cytokines. For example, stimulating dendritic cells in vitro with microbial extracts causes the dendritic cells to rapidly begin producing IL-12. IL-12 is a signal that helps send naive CD4 T cells towards a Th1 phenotype. The ultimate consequence is priming and activation of the immune system for attack against the antigens which the dendritic cell presents on its surface. However, there are differences in the cytokines produced, depending on the type of dendritic cell. The plasmacytoid DC has the ability to produce large amounts of type-1 IFN's, which recruit more activated macrophages to allow phagocytosis.

Given their unique role in initiating primary immune responses, vaccine products prepared from patient-derived cultured DC are under development in a broad range of permutations (Galluzi et al., 2012). Such products can be prepared from peripheral blood or from bone marrow, and form part of the vaccine arsenal that is being evaluated in cancer patients (Palucka et al., 2011). Such DC based vaccines have shown to be safe and well-tolerated, and they do induce antigen-specific $CD4^+$ and $CD8^+$ effector T-cells responses in some patients. Nevertheless, efficacy of such products has been documented in only limited patient numbers, and they have not generated consistent clinical success. This is mainly attributable to the fact that the potency of such patient-based products is impossible to standardize. It is feasible to develop standard operating procedures for harvesting dendritic cell precursors from blood or bone marrow and for subsequent generation functional dendritic cells, but patient-to-patient variability with respect to functional differences will always preclude full reproducibility. Furthermore, there are substantial hurdles for large scale implementation of such patient-based products, since production is laborious, time-consuming and therefore expensive. In addition, there are indications for an inferior T cell-stimulatory phenotype of DC derived from advanced cancer patients, which would also argue against the use of autologous DC. Novel approaches for dendritic cell vaccines are therefore urgently needed.

One way of overcoming these drawbacks would be to generate DC products from sustainable cell lines that could be applied as allogeneic products. This would bypass the need to harvest dendritic cells from individual patients, and allow the production of precisely characterized, predictable and consistent dendritic cell products. In order to qualify for a commercial scale manufacturing process, such a cell line would need to have the following characteristics. First of all the cell line should be clonal and easy to maintain in culture. It also should have reproducible population doubling times, and consistent behavior with respect to responsiveness to differentiation and maturation signals to generate mature functional DC.

A number of cell lines have been explored for this purpose, including KG-1, THP-1, HL-60 and MUTZ-3 (Larsson K., et al., 2006 van Helden et al., 2008 and references therein). From these cell lines, only MUTZ-3-derived DCs closely resemble primary DCs prepared from blood (Larsson et al., 2006 van Helden et al., 2008, Santegoets et al., 2006a, 2006b, and Masterson et al., 2002). Notwithstanding the fact that these cell lines recapitulate some of the antigen presentation and other immunological features of dendritic cells, their limitations in biological and reproducible behavior prohibit their application as the basis for DC vaccines.

There remains a need in the art for cells and cell lines that may be employed in an industrial setting for the production of effective dendritic cells.

SUMMARY OF THE INVENTION

The above mentioned disadvantages have been overcome by providing a cell line, tentatively called DCOne. This cell line has been deposited at the Deutsche Sammlung von Mikroorganismen and Zellkulturen GmbH (DSMZ or German Collection of Microorganisms and Cell Cultures) at Inhoffenstraβe 7 B, 38124 Braunschweig, Germany under accession numbers DSMZ ACC3189 on Nov. 15, 2012.

In one aspect, the invention therefore relates to a cell line as deposited with the DSMZ under accession number DSMZ ACC3189.

The invention also relates to a method for obtaining mature dendritic cells comprising the steps of providing a cell line comprising progenitor cells as described herein, incubating the cell line under conditions that allow differentiation of the progenitor cells into immature dendritic cells and incubating said immature dendritic cells under conditions that allow maturation of the immature dendritic cells into mature dendritic cells.

The invention therefore also relates to mature dendritic cells obtainable by the methods as described herein.

Such mature denfritic cells may be used in the therapy of a number of diseases as further detailed herein below. The invention therefore also relates to mature dendritic cells as described herein for use as a medicament Such mature denfritic cells may be also used as a therapeutic vaccine for a number of diseases as further detailed herein below. In particular, the invention therefore also relates to mature dendritic cells as described herein for use as a therapeutic cancer vaccine.

DETAILED DESCRIPTION OF THE INVENTION

DCOne is a precursor cell line for dendritic cells also known as a progenitor cell line. The DCOne cell line has been derived from the peripheral blood of a patient with acute myeloid leukemia (AML) FAB M4. DCOne progenitor cells are CD34 positive (CD34+) and CD1a negative (CD1a−) as well as CD83 negative (CD83−), see also FIG. 1. Furthermore, they are low in expression or even lack a number of other receptors associated with DC differentiation and maturation, including DCSign, Langerin, CD40 and CD80. Most importantly, DCOne progenitor cells express WT-1 protein as detailed in example 3 and shown in FIG. 2.

DCOne cells may be multiplied in conventional cell culture systems typically used for expansion of hematopoietic cell lines. A typical example of such a culture system comprises MEM-α medium containing FCS, supplemented with GM-CSF, L-Glutamine, and Penicillin/streptomycin. In more detail, the culture system may comprise MEM-α medium containing FCS (10-20%), supplemented with GM- CSF (range 20-40 IU/ml)), L-Glutamine (2 mM), and Penicillin/Streptomycin (100 IU/ml; 100 µg/ml). A particular suitable culture system may comprise MEM-α medium containing 20% FCS, supplemented with GM-CSF (25 IU/ml), L-Glutamine (2 mM), and Penicillin/streptomycin.

The cells may be stored at a concentration of 2.5*10E6 cells/ml in 12.5% DMSO and 87.5% FCS in nitrogen. The process of multiplying DCOne cells is also referred to herein as proliferation of the cells.

Figure 3:
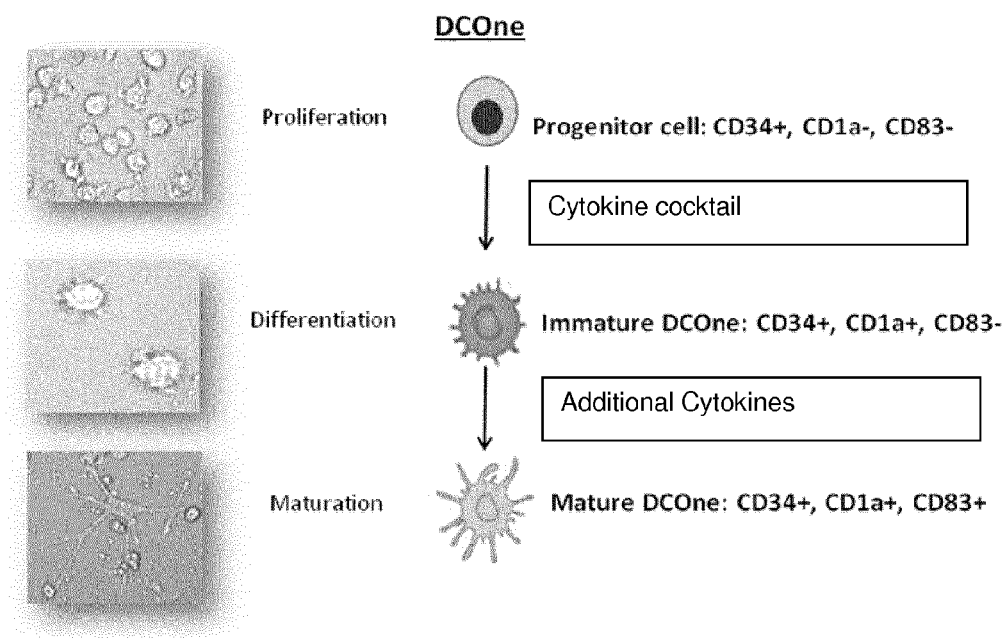

To generate functional, mature dendritic cells from DCOne progenitor cells, DCOne progenitor cells have to undergo a process of stimulation with the appropriate stimulatory molecules. The skilled person will be aware of the metes and bounds of this process of stimulation also known as differentiation and maturation. An example of such a process is illustrated in FIG. 3.

The invention therefore also relates to a method for obtaining mature dendritic cells comprising the steps of providing DCOne cells, incubating the cells under conditions that allow differentiation of the DCOne cells into immature dendritic cells and incubating said immature dendritic cells under conditions that allow maturation of the immature dendritic cells into mature dendritic cells.

The skilled person is well aware of the conditions that allow the differentiation of progenitor cells into immature dendritic cells. For that purpose, the cells may be contacted with the appropriate stimulatory molecules. The term "stimulatory molecules" relates to compounds capable of inducing differentiation and/or maturation of the cells. Such compounds, alone or in specific combination, can induce, when present in sufficient amounts in for example culture medium, the differentiation and/or maturation of dendritic precursor cells, like the above described CD34 positive cells, into or towards dendritic cells.

Well known examples of stimulatory molecules that may be used for the differentiation of progenitor cells into immature dendritic cells include, cytokines such as IL-4 (Interleukin 4), IL-6, PGE-2 (Prostaglandin E2), TNFalpha (Tumour Necrosis Factor Alpha) and TGF-beta(transforming growth factor beta). Also known are growth factors such as GM-CSF (Granulocyte-macrophage colony-stimulating factor). Also described are surrogate molecules for cytokines or growth factors which induce a biological effect comparable to that of the above stimulatory molecules. Such surrogate molecules include antibodies and other biological molecules such as lipopolysaccharides (LPS) and Polyinosinic-polycytidylic acid (polyIC). For a review, see Bürdek et al. Journal of Translational Medicine 2010, 8:90.

The person skilled in the art is equally well aware of methods available in the art for obtaining mature dendritic cells from the immature dendritic cells described above. For example, immature dendritic cells may be matured by contacting the immature dendritic cells with stimulatory molecules, such as TNF-alpha, IL-6, IL-1 beta and/or PGE2, although other methods known in the art to mature immature dendritic cells can likewise be employed. Such treatment will allow for obtaining mature dendritic cells from immature dendritic cells.

The cells thus obtained were found to be fully functional as dendritic cells as is corroborated by our finding that the obtained cells express high levels of MHC Class I, MHC Class II and CD83, the latter being a typical marker for mature DCs (FIG. 1). Such mature DC have the capacity to prime an immune response (Palucka et al., 2011 and Ueno et al., 2010). The cells are therefore suitable for use in a vaccine, more in particular a therapeutic vaccine, such as a therapeutic cancer vaccine.

As used herein, the term vaccine or therapeutic vaccine, in its singular or plural form, refers to medicines that belong to a class of substances known as biological response modifiers. Biological response modifiers work by stimulating or restoring the immune system's ability to fight infections and disease. Therapeutic vaccines are intended to treat an existing cancer by strengthening the body's natural defenses against the cancer.

Figure 2:
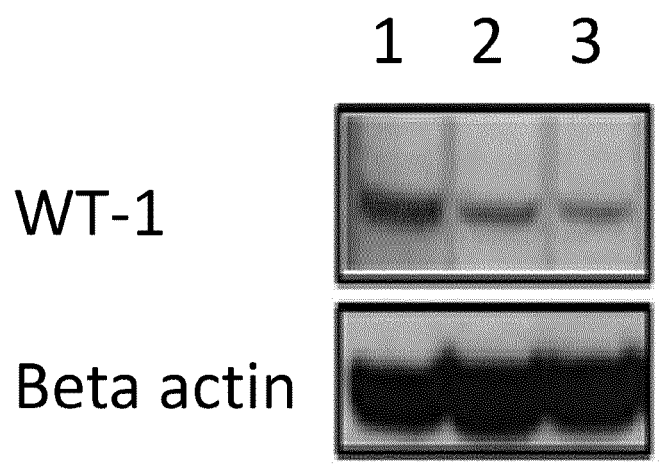

Immature dendritic cells derived from DCOne (hereinafter referred to as iDCOne or immature DCOne) are characterized by the appearance of expression of CD1a. Also other markers begin to be expressed, including DCSign, Langerin, CD80 and CD40. CD83 however remains absent or at very low expression, and this is a hallmark of their status of immature DCs. In addition, iDCOne cells also express WT-1 (FIG. 2).

Mature DCOne cells (mDCOne) are characterized by the appearance of expression of CD83, while the other cell surface receptors such as CD34 and CD1a (CD34+ and CD1a+) remain present as well, albeit that their level of expression may decrease. CD83 expression is the specific hallmark of mature DCs. The expression of other relevant markers is also shown in FIG. 1. Most importantly, mDCOne also express WT-1 (FIG. 2), a well-known tumor antigen.

The invention therefore also relates to mature dendritic cells obtainable from a DCOne cell.

Mature dendritic cells are known in the art. They may conventionally be derived from hematopoietic bone marrow progenitor cells or from peripheral blood mononuclear cells (PBMCs). In an alternative, mature dendritic cells may also be derived from distinct cell lines such as MUTZ-3, HL-60, THP-1 and KG-1 (Larsson et al., 2006, van Helden et al., 2008, Santegoets et al, 2006, and Masterson et al, 2002).

Mature Dendritic cells derived from DCOne progenitor cells were found to be different from dendritic cells known in the prior art and to have several advantageous properties over other mature dendritic cells known in the prior art.

First, in comparison to dendritic cells derived from monocytes termed moDCs herein, mDCOne express at least one tumour-associated antigen, WT-1 (FIG. 2). A conventional dendritic cell derived from blood from a healthy subject does not endogenously express such a tumour antigen and a conventionally derived dendritic cell would therefore have to be loaded with a specific tumour antigen in order to program the dendritic cell to stimulate an immune response against this specific tumour antigen. In contrast, mature DCOne cells can trigger T cells specific for WT-1 directly, thus without the need for deliberate loading. WT1 is overexpressed in a majority of cancers, in particular in AML patients in which 90% of patients overexpress WT-1. WT1 vaccination with peptide vaccines can elicit specific T-cell responses which have been demonstrated in published clinical studies, to exert an anti-tumor effect (van Tendeloo et al., 2012; Krug et al., 2010; Rezvani et al., 2008; May et al., 2007; Rezvani et al., 2005). Several clinical studies in e.g. AML patients with WT1-loaded autologous DC vaccines have also documented immunological responses and clear clinical responses. Its expression in mature DCOne cells is therefore a distinguishing feature of DCOne's potential to function as an antigen presenting vehicle for patients with WT-1 positive tumors, such as patients with AML.

Figure 4:
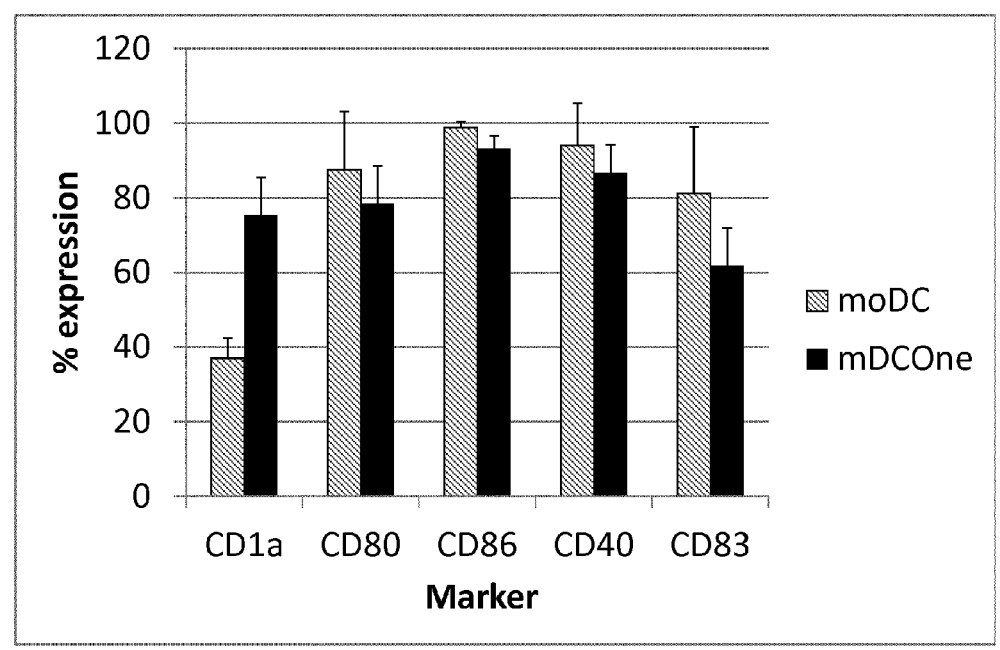

In addition, it was found that mDCOne express about 2 times more CD1a than DCs derived from PBMCs (FIG. 4). CD1a is known to be up-regulated during the process of myeloid DC differentiation, and CD1a molecules represent an important antigen receptor on DC, in particular for lipid antigens. These CD1a molecules then present antigen-derived components to T cells.

Figure 5:
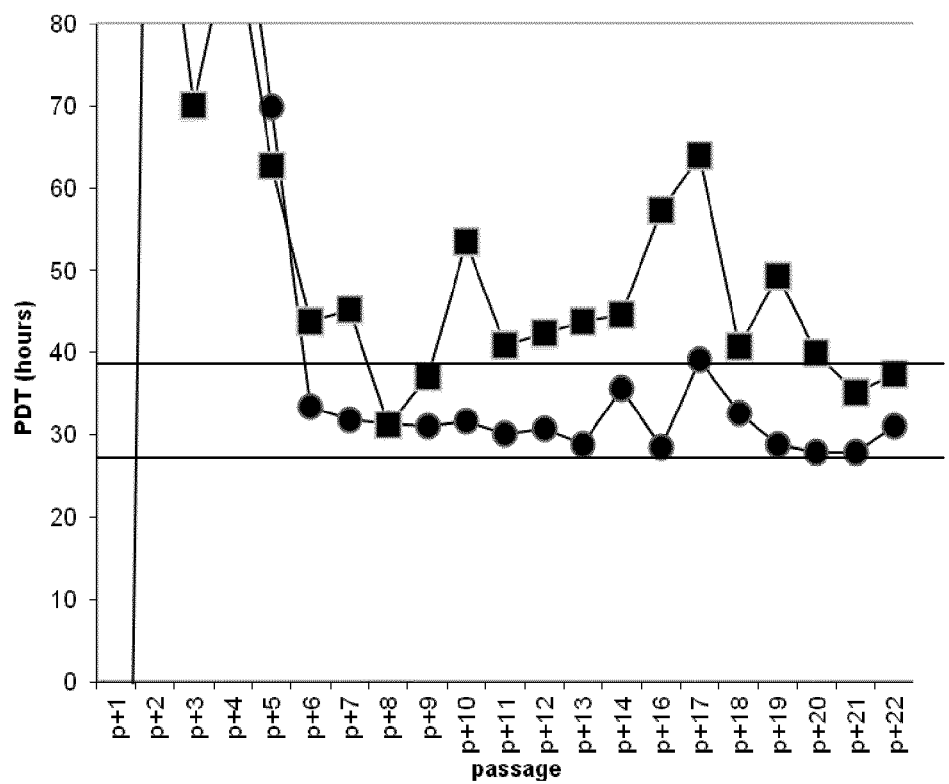

Another advantage relates to an important difference with dendritic cells derived from a cell line termed MUTZ-3. The MUTZ-3 cell line may be obtained from the DSMZ under accession number DSMZ ACC295. We compared the MUTZ-3 cell line to the DCOne cell line as deposited. It appeared that MUTZ-3 cells could not be reproducibly propagated, since the doubling time of these cells varied within unacceptable limits for an industrial or commercial process (FIG. 5). Whereas the doubling time for a DCOne cell culture stayed within the limits of 28-39 hours from the 6$^{th}$ passage on, the doubling time of MUTZ-3 cells varied between 31 and 65 hours. MUTZ-3 are therewith unsuited for a controlled industrial process wherein reproducibility is of key importance and a prerequisite for regulatory authorities. The exact experimental details are provided in Example 4.

We were also able to establish that the DCOne cells as deposited were different from MUTZ-3 in that DCOne has a large aberration from 11p15.5 to 11p12, encompassing approximately 16 Mb of genomic regions (20.7 Mb-36.6 Mb). The heterozygous loss contains close to 60 known and unknown genes. This makes the DCOne cell distinctly different from the MUTZ-3 cell line. The experimental details of this analysis are provided in Example 9.

Figure 6:
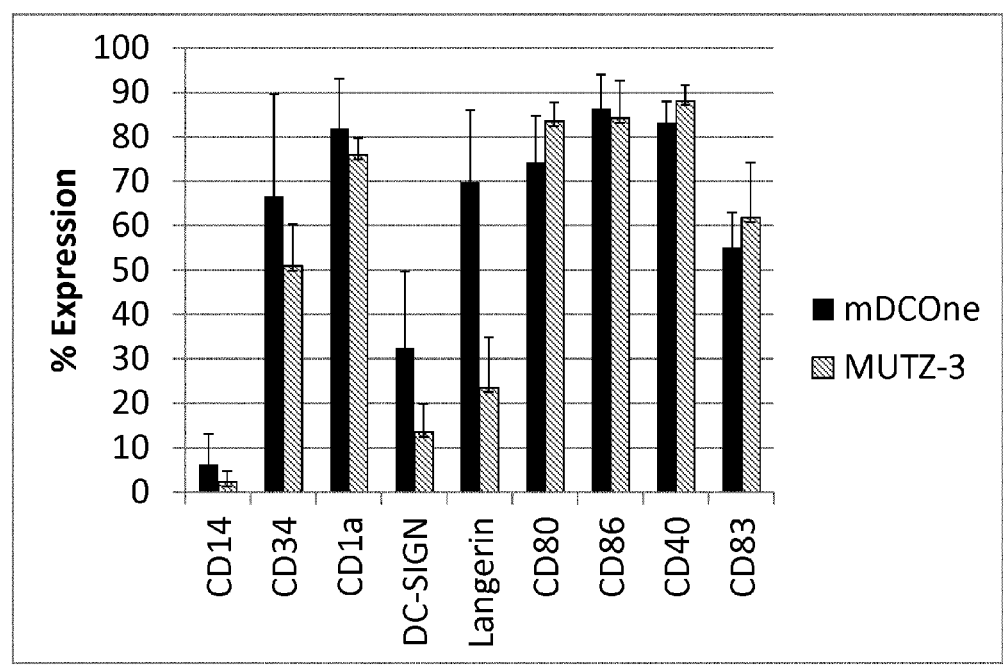

It was also established that mDCOne cells consistently expressed Langerin at a much higher level than MUTZ-3. FIG. 6 shows that about 70% of DCOne cells expressed Langerin whereas less than 25% of MUTZ-3 cells expressed this marker. Experimental details of this analysis are provided in Example 8. Langerin is an important receptor for antigens expressing certain glycan molecules and involved in the uptake and processing of such antigens.

Mature DCOne cells were found to be particularly suited for use as a medicament, particularly for the treatment of cancers, more in particular AML. This is based on the following observations.

Mature DCOne cells endogenously express at least one tumor antigen, selected from the group consisting of WT-1, RHAMM and PRAME, p53 and Survivin. WT-1 is expressed in a large number of cancers, (Rezvani et al, 2005). This makes the mDCOne cells particularly suited for the treatment of different kinds of cancers, including lung cancer, breast cancer, head and neck cancer, chronic myeloid leukemia, ovarian cancer, colon cancer, multiple myeloma, prostate cancer, skin cancer, myelodysplastic syndrome, brain cancer and bladder cancer.

Mature DCOne derived DCs also express HLA-A2, HLA-A3, and HLA-B44 molecules that allow expression of peptides derived from tumor antigens such as WT-1, to be presented to T cells. Moreover, mDCOne expresses an optimal profile of co-stimulatory molecules which allows priming of naïve T cells and reactivating existing effector memory T cells. These co-stimulatory molecules include CD1a-CD40-CD80-CD83-CD86-CD209, as well as other functionally relevant molecules such as HLA-DR and DCSign and Langerin.

Figure 7:
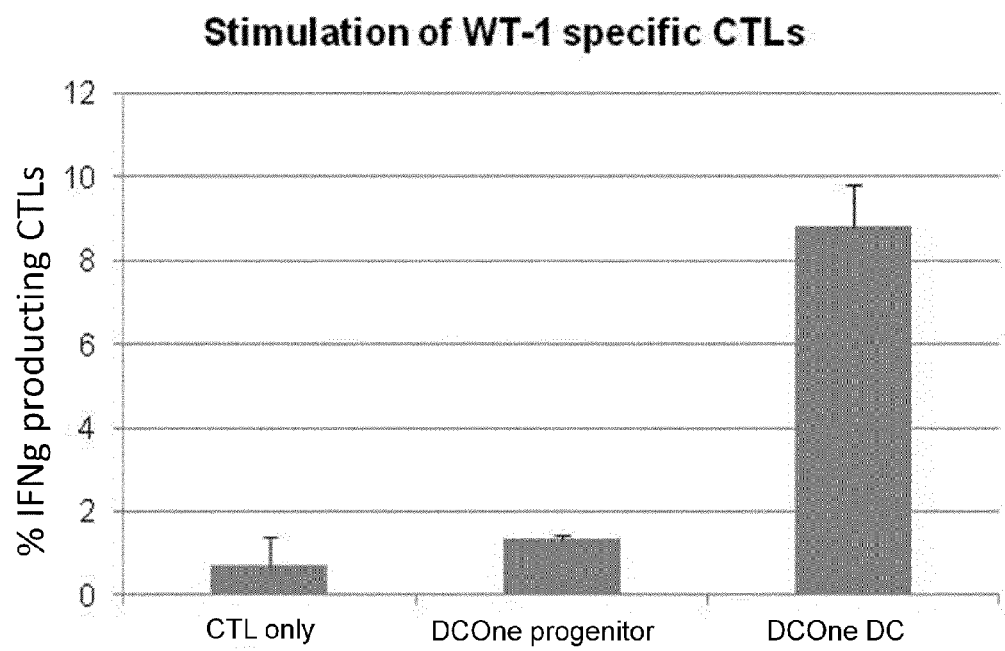

Additionally, we found that the endogenously expressed tumour antigen WT-1 (FIG. 2) in mDCOne cells can activate WT-1-specific T-cells to produce gamma interferon (γIFN), as further detailed in Example 5 and shown in FIG. 7. Mature DCOne are therewith particularly suited for the treatment of patients with AML since ninety percent of AML patients expresses WT-1 antigen. This was further documented by the demonstration that leukemic cells can be killed by WT-1 specific T cells after stimulation with mDCOne cells. This is exemplified in Example 5 and FIG. 8.

It was also found that mDCOne have the ability to migrate to the lymph nodes, which is reflected in its CCR7 expression and in its ability to migrate in vitro to chemokines 6Ckine (also known as CCLL21) and MIP3b (also known as CCL19). This is described in Example 6 and FIG. 9. Indeed it was demonstrated that mDCOne are capable of migrating to chemokines in an in vitro migration assay, reflecting migration to para-cortical T cell areas of lymph nodes.

Figure 10:
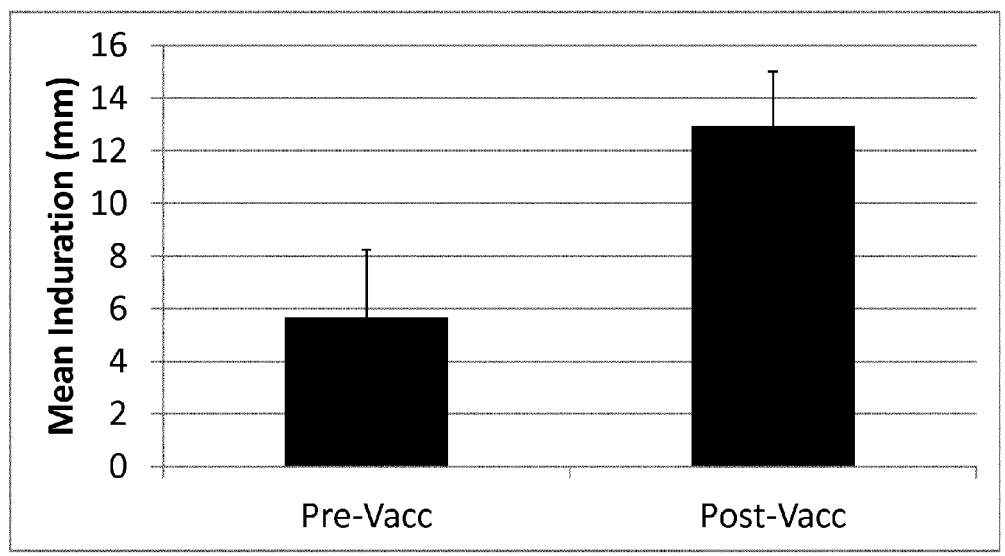
Figure 10:
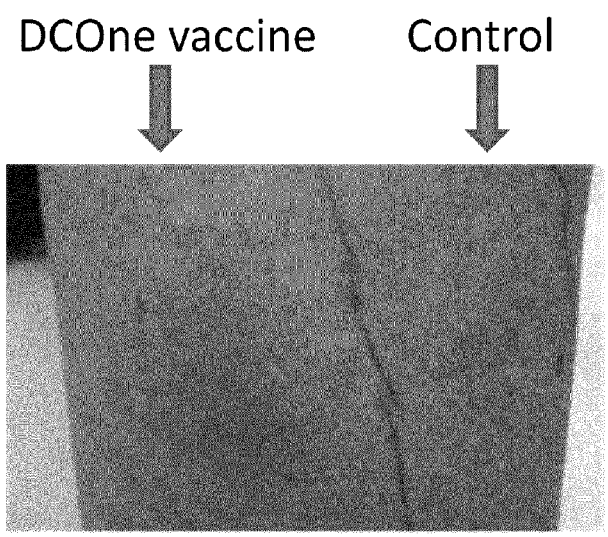

Most importantly, we were able to demonstrate that vaccination with mDCOne in patients with leukemia induced a clinical T-cell response. We observed that vaccinated patients respond with an increased delayed type hypersensitivity response to a re-challenge with mDCOne, as shown in FIG. 10. The swelling and induration observed are accompanied by infiltration of CD4 and CD8 T cells, indicative of a systemic immune response. This is detailed in Example 7.

Figure 11:
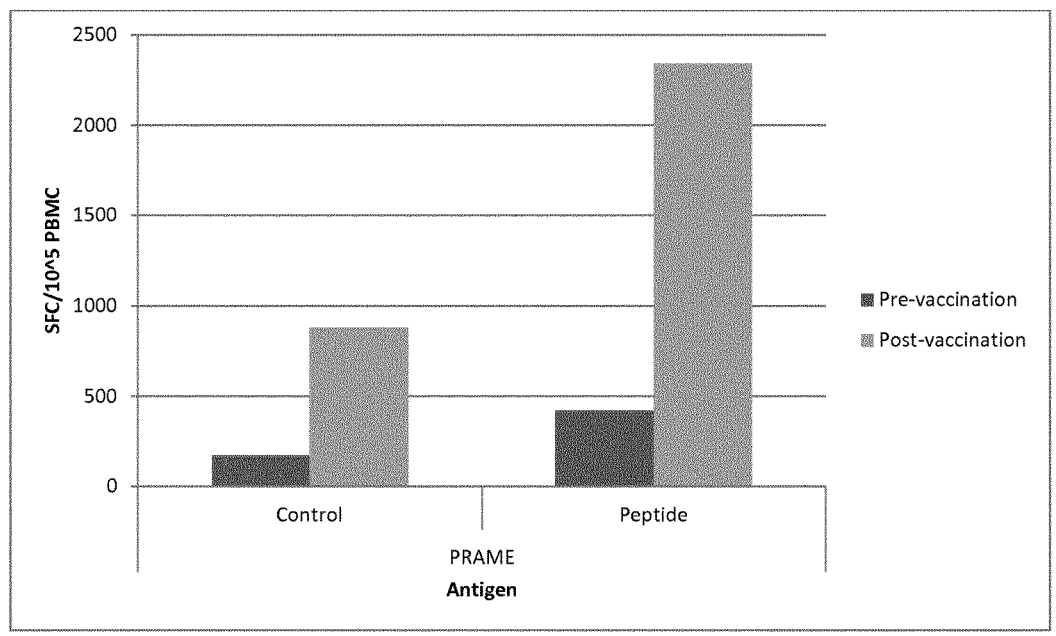

In addition, we observed that vaccination with mDCOne in leukemia patients resulted in an increase in PRAME reactive IFN-γ producing T-cells which is indicative for vaccination induced tumor specific T-cell responses as shown in FIG. 11. These data show that DCOne is capable of inducing a tumor-specific immune response.

Mature DCs, the precursor cells thereof at a suitable stage of differentiation, or the cells of the cell lines as described herein may be loaded with at least one antigen. Such loading may be accomplished using methods known in the art, e.g. by loading with tumor antigens or infection antigens, synthetic or purified or partially purified from biological material, with cell lysates of tumor cells, tumor cell lines, infected cells or cell lines, by fusion with other cells or cell lines, by introducing at least immunotherapeutic gene, by infection with infectious particles or portions thereof. Optionally, the loaded cells or cell lines are subjected to further differentiation by stimulatory molecules. In general, the mature DCs will process the antigens, present them to the corresponding immune cells of the immune system via particular molecules, e.g. via MHCI or MHCII molecules, thereby correspondingly activating the humoral and/or cellular immune response which combats the disease or builds up an immunological memory preventing diseases in a prophylactic fashion. For this purpose, the mature DCs are used as immunotherapeutic agent in the patient.

According to a further aspect of the invention, a method is provided for obtaining mature dendritic cells derived from the DCOne cell line with an altered phenotype. Such a method consists of the steps as described above, such as incubating the DCOne cell line under conditions that allow differentiation of the progenitor cells into immature dendritic cells and incubating said immature dendritic cells under conditions that allow maturation of the immature dendritic cells into mature dendritic cells, additionally comprising a step of altering the phenotype of the mature dendritic cells by introducing genetic material into the cells and/or by knocking out endogenous genes of the cells.

Introduction of genes is understood to be transfection or viral infection or transformation of cells or cell lines, thereby introducing genetic material into the cell or cell lines according to per se known methods. The genetic material can be DNA or RNA. The genetic material codes for the expression of at least one protein or peptide, or/and the RNA itself can have an inhibitory or stimulatory effect, e.g. as an antisense RNA. The proteins being expressed can be further processed and modified, e.g. by glycosylation. Genes can also be introduced by fusing cells or cell lines with other cells or cell lines.

In another aspect of the invention, immunotherapeutic agent genes are introduced into the cells according to the invention. Immunotherapeutic agent genes are genes encoding proteins and/or peptides which play a role in the use of the effective dendritic cells as immunotherapeutic agents, e.g. tumor antigens, viral antigens or antigens from parasites, bacteria or other microorganisms.

Cells or cell lines having immunotherapeutic agent genes incorporated therein will express the proteins or peptides of these genes, and these are presented to the immune system by the dendritic cells, so that the effective dendritic cells activate, inhibit or modulate corresponding immune responses, depending on the activity and effector stages of the effective dendritic cells. For presentation of the gene products, the expressed proteins or peptides are processed or directly used; furthermore, the expressed proteins or peptides can be modified, e.g. by glycosylation.

As used herein, the term tumor antigen refers to peptides, proteins, lipids, lipopeptides, lipoproteins, carbohydrates, glycolipids, glycopeptides, glycoproteins, phosphorylated proteins, phosphorylated peptides, proteins or peptides otherwise modified following translation, which, compared to normal tissue, are overexpressed in the cells of the tumor, underexpressed, expressed de novo, mutated, differentially modified after translation, differentially processed, differentially situated, differentially folded, or otherwise modified.

LEGEND TO THE FIGURES

FIG. 1: Graphic representation of the expression profile of dendritic cell differentiation markers and maturation markers on DCOne progenitor cells, immature DCOne cells and mature DCOne dendritic cells.

FIG. 2: Expression of WT-1 by DCOne derived cells. Photographic representation of a Western blot analysis demonstrating protein expression of WT-1 in DCOne progenitors (lane 1), immature DCOne (lane 2) and mature DCOne dendritic cells (lane 3). An anti-actin antibody is used as the control, showing equivalent protein loading in each lane.

FIG. 3: Schematic representation of the process of proliferation, differentiation and maturation of DCOne cells leading to fully functional DCOne Dendritic Cells.

FIG. 4: Graph representing the percentage expression of various cell markers found on mature DCOne dendritic cells (mDCOne) versus peripheral blood monocyte derived dendritic cells (moDC).

FIG. 5: Graph showing the population doubling time (PDT) of MUTZ-3 progenitor cells (squares) versus DCOne progenitors (circles). Horizontal axis represents passage numbers.

FIG. 6: Graph showing the expression of different cell markers in mature DCOne (mDCOne) and MUTZ-3 cells.

FIG. 7: Graph showing the stimulation of WT-1 specific Cytotoxic T-lymphocytes by mDCOne as demonstrated by IFN release.

Figure 8:
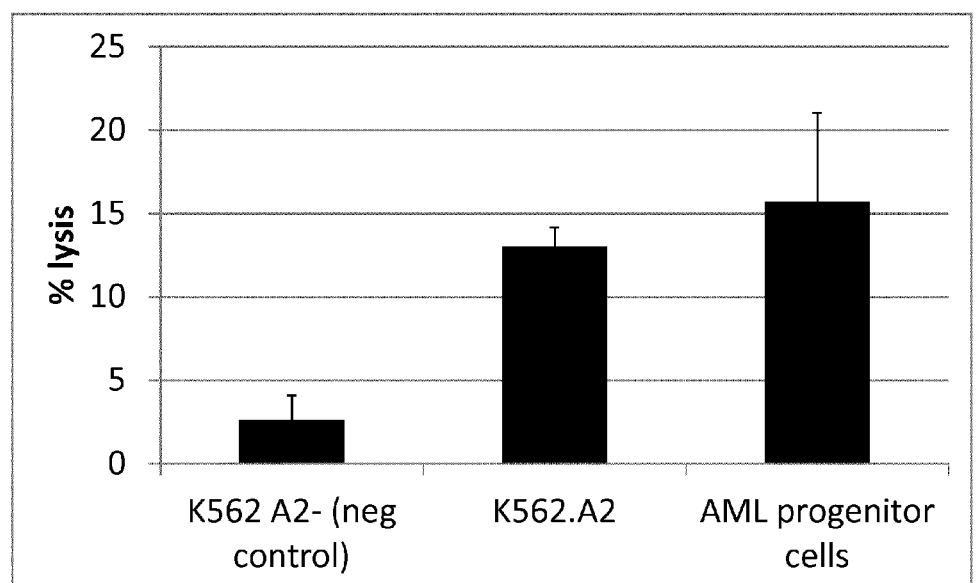

FIG. 8: Graph showing percentage lysis of target cells by WT-1 specific cytotoxic T-lymphocytes (CTL) that have been stimulated by mDCOne. Such stimulated CTL specific for WT1 can kill cells of the myeloid leukemia cell line K562 when K562 is transfected with HLA-A2, since HLA-A2 is required for WT-1 antigen presentation. As a negative control, the untransfected K562 cell line that lacks HLA-A2 was used. Also cells from another AML cell line, AML progenitors, could be killed.

Figure 9:
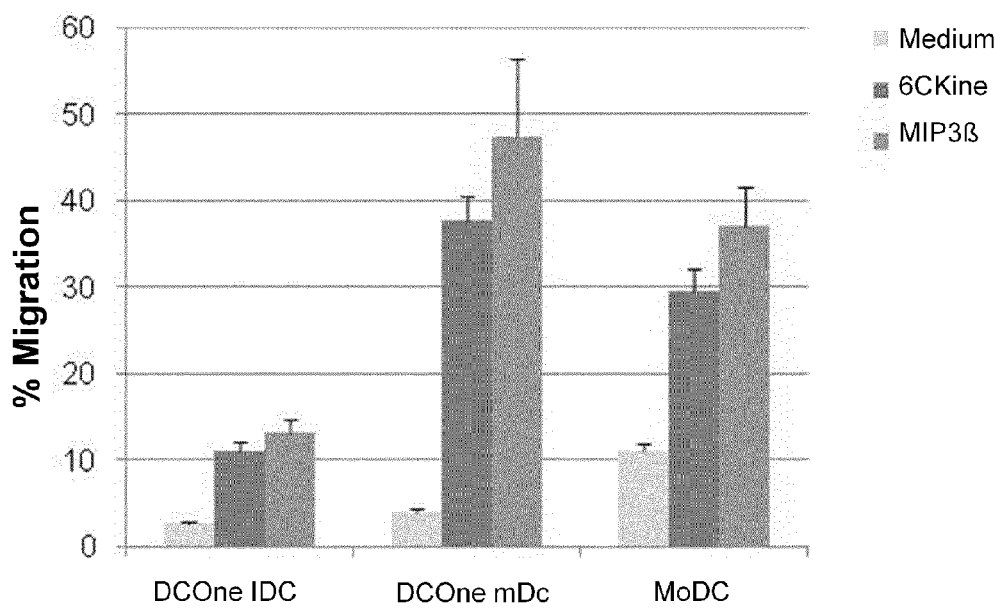

FIG. 9: Graph showing the percent migration of immature DCOne, mature DCOne and monocyte derived dendritic cells under the influence of two lymph node homing cytokines (6Ckine (CCL21) and MIP3beta (CCL19)). Culture medium is used as the control.

FIG. 10: Graph and photograph showing the relation between mean induration and pre- and post vaccination potential of mDCOne cells to induce a systemic immune response in patients, as documented by the delayed type hypersensitivity (DTH) response (Upper Panel). Picture showing a typical delayed type hypersensitivity response as documented by erythema and induration (Lower Panel). As a negative control, the formulation fluid used to cryopreserve mDCOne cells is used.

FIG. 11: Pre- and post-vaccination PBMC were in-vitro stimulated with PRAME peptide mix and cultured for 10 days. The cells were restimulated with PRAME peptides and PRAME reactive IFN-γ-producing T-cells were analysed in IFN-γ ELISpot assay. Medium control served as negative control.

EXAMPLES

Example 1

Proliferation, Differentiation and Maturation of DCOne Cells

DCOne progenitor cells may be differentiated into cells with all characteristics of immature dendritic cells, and subsequently matured into cells with all characteristics of mature dendritic cells.

DCOne progenitor cells were cultured (expanded) in routine maintenance medium, consisting of MEM-α (Minimum essential medium, Lonza, Verviers, Belgium) containing 10% fetal calf serum (FCS) (Hyclone, Perbio Science, Etten-Leur, The Netherlands), 100 IU/ml sodium-penicillin (pen), 100 µg/ml streptomycin (strep), 2 mM L-glutamine (glut), 50 µM β-mercaptoethanol (2ME) and GM-CSF (5 ng/ml). This is the first step, resulting in expansion of the progenitor cells.

Progenitor cells were allowed to differentiate into immature DCOne for 6 days by adding 1000 IU/ml GM-CSF, 20 ng/ml IL-4 and 120 IU/ml TNF-α. Fresh cytokines were added on day 3.

Next, maturation was induced by adding mimic mix (2400 IU/ml TNF-α, 100 ng/ml IL-6, 1 ug/ml PGE2 and 25 ng/ml IL1-β) for 2 days.

Example 2

Phenotyping

Cells were immunophenotyped using the following FITC- and/or PE-conjugated Mabs reactive against: CD1a (1:25), CD80 (1:25), CD86 (1:25), CD40 (1:10) (PharMingen, San Diego, Calif.), CD14 (1:25), DC-SIGN (1:10) (BD Biosciences, San Jose, Calif.), CD83 (1:10), CD34 (1:10), Langerin (1:10) (Immunotech, Marseille, France). 2.5 to 5·10$^4$ cells were washed in PBS supplemented with 0.1% BSA and 0.02% NaN$_3$ and incubated with specific or corresponding control Mabs for 30 minutes at 4° C. Cells were washed and analyzed on a FACS-Calibur flow cytometer (Becton and Dickinson, San Jose, Calif.) equipped with CellQuest analysis software. Results were expressed as the percentage of positive cells. Mature DCOne cells exhibit the prototypical expression of the mature DC marker CD83, and strongly increased expression of CD1a and CD40, as can be observed in FIG. 1.

Example 3

Comparison with Dendritic Cells Prepared from CD34+ Precursor Cells

The phenotypical characteristics of mature DCOne cells are comparable to those of mature dendritic cells prepared from CD34+ precursor cells. CD34+ haematopoietic precursor r cells were isolated from blood of healthy donors and expanded for 2-5 weeks with 25 ng/ml fms-like tyrosine kinase-3 ligand (Flt3-L) and 10 ng/ml stem cell factor (SCF). Thereafter, they were differentiated and matured as described above. This process is illustrated in FIG. 3. DCOne progenitor cells were expanded, differentiated and matured as described above using medium supplemented with specific cytokines. Cells were subsequently tested using flow cytometry for expression of the markers CD1a, CD80, CD86, CD40 and CD83, using antibodies as described under Example 2. The phenotypic characteristics of the monocyte-derived mature DC population and mature DCOne cells are comparable, as can be seen in FIG. 4. Mature DCOne showed a higher expression of CD1a in comparison to moDC. CD1a is a characteristic molecular marker on DCs that are differentiated and is involved in antigen-presenting functions. MoDCs and DCOne were comparable in their expression of CD80, CD86, CD40 and CD83. CD83 is a co-stimulatory molecule and is the most specific marker of mature DCs, since it is absent from immature DC (see also FIG. 1).

Example 3

DCOne as Well as iDCOne and mDCOne Express WT-1

Western blotting was performed with a commercial SDS-PAGE Electrophoresis System. Cells (10E6) were lysed in RIPA buffer (50 mM Tris, 150 mM NaCl, 0.1% SDS, 0.5% sodium deoxycholate, 1% Triton X100 and proteinase inhibitor PMSF)

Ten microgram protein samples were resuspended in a reduced SDS PAGE sample buffer, and then electrophoresed on 4 to 10% Tris gel with Tris running buffer and blotted to PVDF membrane. The blots were blocked for 1 hour at room temperature in 10% non-fat dry milk in Tris buffered Saline containing 0.1% Tween-20 (TBST). Blots were probed with a polyclonal anti WT-1 antibody diluted in TBST containing 0.5% non-fat dry milk in TBST. A horseradish peroxidase-conjugated goat anti-rabbit antibody was then added, and secondary antibodies were detected through autoradiography using enhanced chemiluminescence (ECL Plus, General Electric Healthcare, Milwaukee, Wis.). Beta actin was used as a protein loading control and detected by an anti-beta actin antibody.

Example 4

Reproducibility of Proliferation of DCOne in Comparison with MUTZ-3

Progenitor cells obtained from the DCOne and MUTZ-3 cell line (obtained from DSMZ) progenitors were cultured in T175 culture flasks at 0.2×10E6 cells/ml in MEM-alpha 20% FCS plus penicillin/streptomycin supplemented with 20% conditioned medium of 5637 supernatant (Kurtzberg et al., 1989 and Welte et al., 1985). Cells are incubated in a CO2 incubator at 37 degrees Celsius+5% CO2 and passed every 3 to 4 days. Population Doubling Times (PDT) were assessed by cell counting.

To obtain conditioned medium from 5637 cells, 5637 cells of a growing and confluent culture were seeded at 0.9×10E6 cells/25 ml/T175 culture flask and incubated in a CO2 incubator at 37 degrees Celsius and 5% CO2. After 72 hours, all conditioned medium was collected by centrifugation for 10 minutes at 3000 rpm at 4 degrees Celsius.

Example 5

Activation of WT-1 Specific T Cells

It appeared that mature DCOne cells were able to directly activate WT-1 specific T-cells, without any deliberate loading with WT-1 antigen of exogenous origin, and such WT-1 specific T cells stimulated by the DCOne product can kill WT-1 positive leukemic tumour cells in vitro.

Due to its WT-1 expression, the mature DCOne product can stimulate WT1-specific T cells as demonstrated by their ability to induce IFN release by T-cells specific for WT-1, as well as induce killing of leukemia cells by such DCOne-stimulated WT-1 specific T cells. A sample of the data is shown in FIGS. 7 and 8.

In these experiments, WT-1-specific T cell clones were analysed for cytotoxicity by flow cytometry using K562, K562-A2 and DCOne progenitors as targets labelled with carboxyfluorescein diacetate succinimidyl ester (CFSE; ImmunoChemistry technologies, LLC, MA, USA). In short, 1-2×10E6 target cells were washed and labelled with 1:10 diluted CFSE stock solution for 15 minutes at room temperature (RT). Next, the target cells were washed with 1 ml Iscove's Modified Dulbecco's Media (IMDM, Gibco) supplemented with 100 U/mL penicillin/100 microliter/mL streptomycin, 2 mM L-glutamine (Life technologies, Grand Island, N.Y., USA; further referred as CTL medium). Cells were resuspended in 2 ml CTL medium and incubated in water bath for 30 minutes at 37 degrees Celsius. CFSE-labelled targets cells were then washed and co-cultured with WT-1 specific T cell clones at desired effector:target (E:T) ratios for 4 hours at 37 degreesCelsius in a fully humidified 5% CO2 atmosphere. After 4 hours co-cultured cells were stained with 7AAD for 15 minutes on ice in dark and then analysed on FACSCalibur (BDbiosciences) and the data were analysed using CellQuest software.

Example 6

Migration Assay

Mature DCOne were shown to have the capacity to migrate in response to chemokines that determine their homing to the para-cortical lymph node areas. Mature DCOne cells are equivalent or superior to conventional monocyte-derived DC, as can be seen in FIG. 9. Being able to migrate is an essential feature of DC. For in vitro trans-well migration assays, 10E5 mDCOne cells or MoDC were seeded in the upper compartment of Costar 24-well trans-wells with a pore-size of 6 μm. The lower compartment contained 600 μl serum free MEM-α supplemented with pen/strep, and 250 ng/ml CCL19 (Mip3beta; Pepro-tech, Huissen, The Netherlands) or CCL21 (6CKine; Invitrogen, Carlsbad, Calif.). Cells were allowed to migrate for 4 hours at 37° C. After migration, 500 µl medium was harvested from the lower compartment and migrated cells were quantified with flow-count fluorospheres (Beckman Coulter, Fullerton, Calif.) by flow cytometry.

Example 7

Clinical T Cell Responses in Patients Vaccinated with mDCOne as Measured by Induction of a DTH Response The skin test injections are made on the volar side of the right arm of a human volunteer, at least 5 cm apart from each other, and delayed type hypersensitivity (DTH) reactions. (Induration and erythema areas) were recorded after 48 h, and calculated as circular areas based on the average of vertical and horizontal diameters. The results are shown in FIG. 10.

Example 8

Mature DCOne Cells Express Langerin at a Higher Level than MUTZ-3 Derived Dendritic Cells Cells were immunophenotyped using the following FITC- and for PE-conjugated Mabs reactive against: CD1a (1:25), CD80 (1:25), CD86 (1:25), CD40 (1:10) (PharMingen, San Diego, Calif.), CD14 (1:25), DC-SIGN (1:10) (BD Biosciences, San Jose, Calif.), CD83 (1:10), CD34 (1:10), Langerin (1:10) (Immunotech, Marseille, France). 2.5 to 5×10⁴ cells were washed in PBS supplemented with 0.1% BSA and 0.02% NaN3 and incubated with specific or corresponding control Mabs for 30 minutes at 4 C. Cells were washed and analyzed on a FACS-Calibur flow cytometer (Becton and Dickinson, San Jose, Calif.) equipped with CellQuest analysis software. Results were expressed as the percentage of positive cells.

Example 9

DCOne Cells Carry a Deletion in Comparison with MUTZ-3

We have performed an array comparative genomic hybridization on a 180K array produced by Agilent to test chromosomal commonalities and differences in copy number between DCOne cells and MUTZ-3 cells. The array used is a custom array with probes spaces 17 kb as described by Tack et al 2010.

Cell line DCOne was found to be distinctly different from MUTZ-3 since DCOne has a large aberration from 11p15.5 to 11p12 encompassing approximately 16 Mb of genomic regions (20.7 Mb-36.6 Mb). The heterozygous loss contains close to 60 known and unknown genes. This is considered a large loss and makes the DCOne cell line different from MUTZ-3. We found that the copy number variable regions (CNVs) indicates that the DCOne cell line is clonal, this means that the deletions on 7q and 12p are the same in all cells obtained from the cell line.

REFERENCES

1. Masterson A J, Sombroek C C, de Gruijl T D, Graus Y M, van der Vliet H J, Lougheed S M, van den Eertwegh A J, Pinedo H M, Scheper R J (2002) MUTZ-3, a human cell line model for the cytokine-induced differentiation of dendritic cells from CD34+ precursors. Blood 100:701-703.
2. Santegoets S J A M, Schreurs M W, Masterson A J, Liu Y P, Goletz S, Baumeister H, Kueter E W, Lougheed S M, van den Eertwegh A J, Scheper R J, Hooijberg E, de Gruijl T D (2006) In vitro priming of tumor-specific cytotoxic T lymphocytes using allogeneic dendritic cells derived from the human MUTZ-3 cell line. Cancer Immunol Immunother 55:1480-1490
3. Santegoets S J A M, Masterson A J, van der Sluis P C, Lougheed S M, Fluitsma D M, van den Eertwegh A J, Pinedo H M, Scheper R J, de Gruijl T D (2006) A CD34(+) human cell line model of myeloid dendritic cell differentiation: evidence for a CD14(+)CD11b(+) Langerhans cell precursor. J Leukoc Biol. 80:1337-1344.
4. Tack G J et al., Phenotypic and genomic analysis of an exceptional case of enteropathy associated T-cell lymphoma. Leuk Res. 2010 August; 34(8):e183-9.
5. Cheever et al, Clin Cancer Res 15-5323-2009. The prioritization of cancer antigens: A national cancer institute pilot project for the acceleration of translational research.
6. Vermeij et al, Clinical and Developmental Immunology 2010-891505-2010. Potential target antigens for a universal vaccine in epithelial ovarian cancer.
7. Narita et al, International Journal of Medical Sciences 7-72-2010. WT1 Peptide vaccination in combination with imatinib therapy for a patient with cml in the chronic phase.
8. Greiner et al, Haematologica 95-1191-2010. High-dose RHAMM-R3 peptide vaccination for patients with acute myeloid leukaemia, myelodysplastic syndrome and multiple myeloma.
9. Schmitt et al, Blood 111-1357-2008. RHAMM-R3 peptide vaccination in patients with acute myeloid leukemia, myelodysplastic syndrome, and multiple myeloma elicits immunologic and clinical responses.
10. Baars et al, Annals of Oncology 11-965-2000. Skin tests predict survival after autologous tumor cell vaccination in metastatic melanoma: Experience in 81 patients.
11. Quintarelli et al, Blood 117-335-2011. High-avidity cytotoxic T lymphocytes specific for a new PRAME-derived peptide can target leukemic and leukemic-precursor cells.
12. Kohrt et al, Blood 118-5319-2011. Donor immunization with WT1 peptide augments antileukemic activity after MHC=matched bone marrow transplantation.
13. Greiner et al, Blood 106-938-2005. Identification and characterization of epitopes of the receptor for hyaluronic acid-mediated motility (RHAMM/CD168) recognized by CD8+ T cells of HLA-A2-positive patients with acute myeloid leukemia.
14. Rezvani et al, Clin Cancer Res 11-8799-2005. T-Cell responses directed against multiple HLA-A *0201-restricted epitopes derived from Wilms' tumor 1 protein in patients with leukaemia and healthy donors: Identification, Quantification and characterization.
15. May et al, Clin Cancer Res 13-4547-2007. Peptide epitopes from the Wilms tumor 1 oncoprotein stimulate CD4+ and CD8+ T Cells that recognize and kill human malignant mesothelioma tumor cells.
16. Gao et al, Blood 95-2198-2000. Selective elimination of leukemic CD34+ progenitor cells by cytotoxic T lymphocytes specific for WT1.
17. Ochsenreiter et al, Immunotherapy Journal 34-85-2011. Wilms tumor protein 1 (WT1) peptide vaccination-induced complete remission in a patient with acute myeloid leukemia is accompanied by the emergence of a predominant T-cell clone both in blood and bone marrow.
18. Rezvani et al, Blood 111-236, 2008. Leukemia-associated antigen-specific T-cell responses following combined PR1 and WT1 peptide vaccination in patients with myeloid malignancies.
19. Wadelin et al, Moleculal Cancer 9-226, 2010. Leucine-rich repeat protein PRAME: expression, potential functions and clinical implications for leukaemia.
20. Quintarelli et al, Blood 112-1876-2008. Cytotoxic T lymphocytes directed to the preferentially expressed antigen of melanoma (PRAME) target chronic myeloid leukemia.
21. Schmitt et al, Exp. Hematol 34-1709-2006. Chronic myeloid leukemia cells express tumor-associated antigens eliciting specific CD8+ T-cell responses and are lacking costimulatory molecules.
22. Amir et al, Clin cancer Res 2011 Sep. 1; 17(17):5615-25. Epub 2011 Jul. 19 PRAME specific allo-HLA restricted T-cells with potent antitumor reactivity useful for therapeutic T cell receptor gene transfer.
23. Krug et al, Cancer Immunol Immunother 2010 October; 59(10):1467-79. Epub 2010 Jun. 8. WT1 peptide vaccinations induce CD4 and CD8 T cell immune responses in patients with mesothelioma and non-small cell lung cancer.
24. Van Tendeloo et al, PNAS 2010 Aug. 3; 107(31):13824-9. Epub 2010 Jul. 14 Induction of complete and molecular remissions in acute myeloid leukemia by Wilms' tumor 1 antigen-targeted dendritic cell vaccination.
25. Galluzzi et al., OncoImmunology 1:7, 1-24 (2012) Dendritic cell based interventions for cancer therapy,
26. Kurtzberg, J., et al., (1989) Blood 73, 381-390.
27. Welte, K., et al., (1985) Proc. Nat!. Acad. Sci. USA 82, 1526-1530.
28. Palucka, K., H. et al., 2011. Recent developments in cancer vaccines. *J. Immunol.* 186: 1325-1331.
29. Ueno H, et al., Harnessing human dendritic cell subsets for medicine. *Immunol Rev.* 2010 March; 234(1):199-212.
30. Bürdek et al. Journal of Translational Medicine 2010 8:90 doi:10.1186/1479-5876-8-90.
31. Larsson K., et al., Immunology 117; 156-166 (2006).
32. Van Helden S. F. G. et al., Immunology Letters 117; 191-197 (2008).

The invention claimed is:

1. A composition comprising:
a precursor cell line as deposited at the DSMZ under accession number DSMZ ACC3189 on Nov. 15, 2012; and
a cryopreservative.

2. A composition comprising:
a mature dendritic cell differentiated from a precursor cell line as deposited at the DSMZ under accession number DSMZ ACC3189 on Nov. 15, 2012; and
a cryopreservative.

3. A composition comprising:
a precursor cell line as deposited at the DSMZ under accession number DSMZ ACC3189 on Nov. 15, 2012, or mature dendritic cells differentiated from the precursor cell line; and
a cryopreservative.

* * * * *